United States Patent [19]

Swiggett

[11] Patent Number: 4,485,817
[45] Date of Patent: Dec. 4, 1984

[54] SURGICAL STAPLER APPARATUS WITH FLEXIBLE SHAFT

[75] Inventor: Brian E. Swiggett, Oyster Bay, N.Y.

[73] Assignee: United States Surgical Corporation, Norwalk, Conn.

[21] Appl. No.: 383,129

[22] Filed: May 28, 1982

[51] Int. Cl.³ ............................................. A61B 17/04
[52] U.S. Cl. ................................ 128/334 R; 128/305; 227/DIG. 1
[58] Field of Search ........... 128/334 R, 303 R, 334 C, 128/305, 356, 335; 227/DIG. 1

[56] References Cited

U.S. PATENT DOCUMENTS

| | | | |
|---|---|---|---|
| 2,905,178 | 9/1959 | Hilzinger | 128/303 |
| 3,452,615 | 7/1969 | Gregory, Jr. | 74/501 |
| 3,552,626 | 1/1971 | Astafiev et al. | 227/76 |
| 3,638,652 | 2/1972 | Kelley | 128/305 |
| 3,952,747 | 4/1976 | Kimmell | 128/303 R |
| 4,108,211 | 8/1978 | Tanaka | 138/120 |
| 4,319,576 | 3/1982 | Rothfuss | 128/334 R |
| 4,351,466 | 9/1982 | Noiles | 128/334 R |

FOREIGN PATENT DOCUMENTS

| | | | |
|---|---|---|---|
| 2347418 | 9/1973 | Fed. Rep. of Germany | 128/334 R |
| 1185292 | 3/1970 | United Kingdom | 128/334 R |
| 2016991 | 9/1979 | United Kingdom | 128/334 R |
| 2038692 | 7/1980 | United Kingdom | 128/334 R |
| 266139 | 3/1973 | U.S.S.R. | 128/334 R |

Primary Examiner—John D. Yasko
Assistant Examiner—Gene B. Kartchner
Attorney, Agent, or Firm—John E. Nathan; Robert R. Jackson; Richard A. Inz

[57] ABSTRACT

A surgical stapler comprising a stapling section, an actuator section remote from the stapling section, and a longitudinally flexible shaft connecting the stapling and actuating assemblies is disclosed. The stapling section generates a force to staple tissue responsive to a much smaller force transmitted hydraulically from the actuator section via the flexible shaft.

11 Claims, 7 Drawing Figures

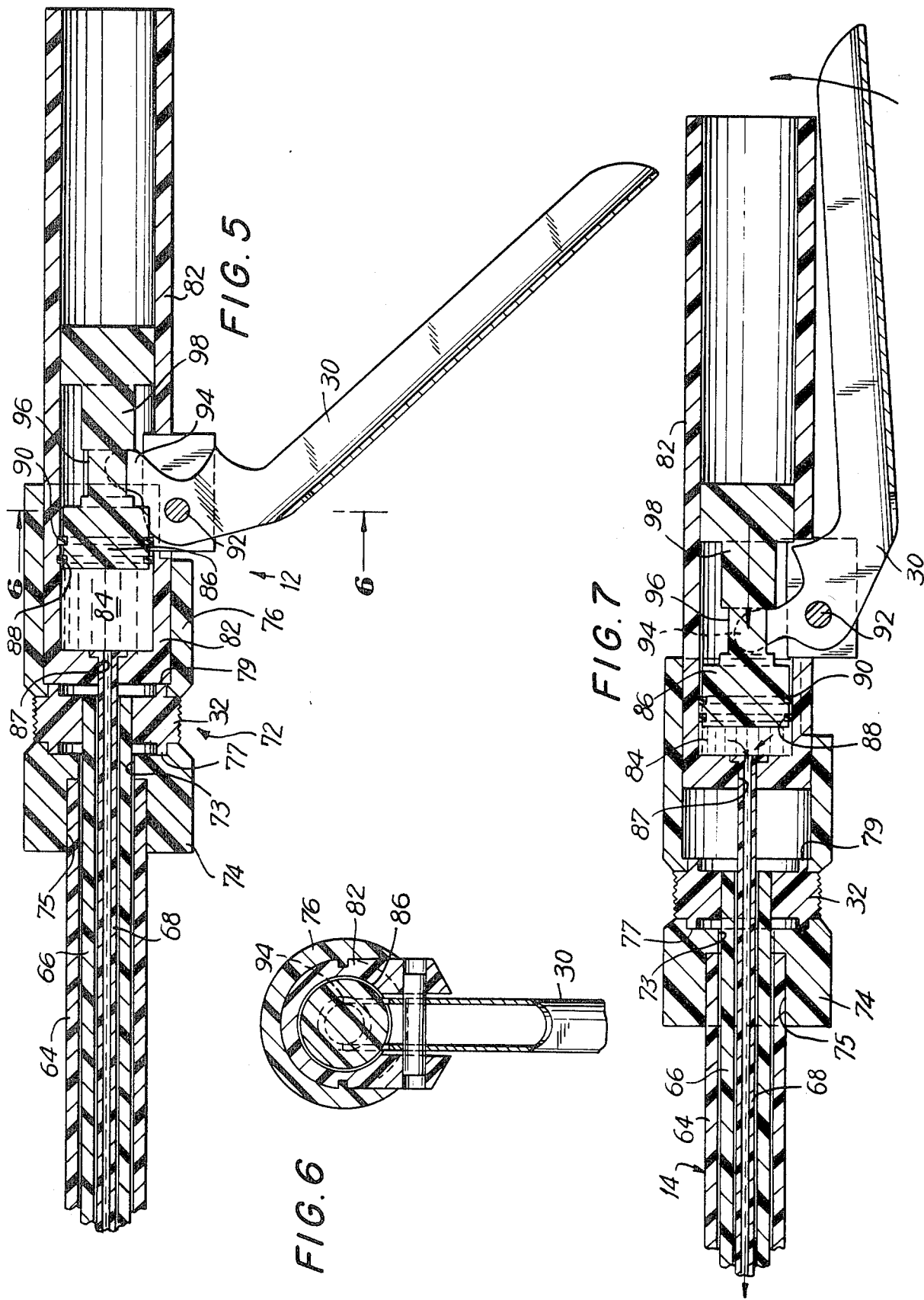

SURGICAL STAPLER APPARATUS WITH FLEXIBLE SHAFT

BACKGROUND OF THE INVENTION

This invention relates to surgical stapler apparatus, and more particularly to surgical stapler apparatus having a longitudinally flexible shaft intermediate the portion of the apparatus which performs the stapling function and the actuator portion of the apparatus. (For simplicity, discussion hereinafter will largely be confined, in terms, to surgical staplers, but it is to be understood that the scope of the invention includes apparatus for applying any type of surgical fasteners.)

There are several known types of surgical staplers in which the stapling function takes place at a location which is relatively remote from the location at which the stapler is held and actuated by the operator. Examples of such staplers are the linear closure surgical staplers shown in U.S. Pat. No. 3,494,533, issued Feb. 10, 1970, to Green et al., and commonly assigned herewith, and the circular anastomosis surgical staplers shown in U.S. Pat. No. 4,304,236, issued Dec. 8, 1981, to Conta et al., and commonly assigned herewith. Typically, in instruments of the types exemplified by these patents, tissue to be stapled is clamped between an anvil assembly and a staple holding assembly, both of which are located at the distal end of the instrument. The clamped tissue is stapled by driving one or more staples from the staple holding assembly so that the ends of the staples pass through the tissue and are clinched by contact with the anvil assembly. The forces required to operate the instrument are applied by the operator of the instrument to one or more actuator elements located at or near the proximal end of the instrument. The distal and proximal portions of the instrument are joined by a longitudinal connecting shaft structure along which the actuating forces and motions are transmitted to the distal operating elements. This type of construction, including relatively widely spaced distal and proximal portions, may be employed for any of several reasons, such as the relative inaccessibility of the tissue to be stapled, or the need to see the tissue well during stapling.

In some applications of instruments of the types mentioned above, it may be desirable for the longitudinal shaft structure joining the distal and proximal portions of the apparatus to have at least a section which can be bent in a direction transverse to the longitudinal axis of the instrument (i.e., which is longitudinally flexible). This may facilitate placement of the instrument in particular body structures, it may facilitate reaching remote or relatively inaccessible stapling sites, or it may allow the staples to be positioned at the stapling site at various angles relative to the operator of the instrument.

The approach taken in the present invention is to transmit only a small force hydraulically along the flexible shaft and to use that force to generate or trigger a larger force in the applicator to apply the staples to the tissue. By localizing the large stapling force in one end of the apparatus, and making the force transmitted along the flexible shaft sufficiently small, the flexible shaft can be kept from straighting significantly during application of the staples.

SUMMARY OF THE INVENTION

It is the principal object of the invention to provide a longitudinally flexible instrument for applying surgical fasteners to tissue.

Another object of the invention is to provide such an instrument in which the large forces required for applying the fasteners are localized in one end of the device.

Another object of the invention is to provide such an instrument having a hydraulic actuation system.

Still another object of the invention is to produce such an instrument that is at least substantially equally flexible in any transverse direction.

According to the present invention, an instrument for applying surgical fasteners comprises an actuator (handle section), an applicator section (including a container for the fasteners, which may be an integral part of the instrument or a separate cartridge, and means for applying the fasteners), and a flexible shaft connecting the actuator and the applicator. The shaft is longitudinally flexible in any direction, and once bent into a given shape, will retain that shape. The apparatus also comprises means for generating a force in the applicator to apply the fasteners responsive to a much smaller actuation force transmitted hydraulically from the actuator via the flexible shaft. The transmission of the actuation force by the flexible shaft is effected in such a manner that it has no significant tendency to straighten the shaft.

In the preferred embodiment, the applicator comprises a fluid chamber one wall of which is defined by a piston connected to a known device for applying the fasteners to tissue, in such a way that movement of the piston in the distal direction actuates the conventional fastener-applying device. Introduction of a hydraulic fluid into the chamber at a sufficiently high pressure moves the piston with sufficient force to cause the fasteners to be applied. The flexible shaft comprises a flexible, small-diameter tube communicating with the fluid chamber and with a similar fluid chamber in the actuator. Preferably, a stiffer, but still flexible, second tube or sleeve containing the small-diameter tube gives the shaft the relatively slight degree of rigidity necessary to enable the flexible shaft to maintain a desired shape into which the shaft has been bent. The fluid, preferably a sterile 0.9% saline solution so that leakage poses no danger of infection, is forced under pressure from the actuator fluid chamber, through the small-diameter tube, and into the applicator fluid chamber by means of a piston in the actuator chamber. The tube has a much smaller diameter than either of the fluid chambers, so that the forces in the tube due to the fluid pressure are much smaller than those on the pistons in the chambers. As a result, the line tension in the tube is minimal, and the slight rigidity of the material or materials of which the shaft is made is sufficient to resist straightening.

In the most preferred embodiment, the fasteners are particularly contemplated to be surgical staples, requiring an anvil as part of the applicator (or as part of a standard staple cartridge used with the apparatus of the invention). In operation, the tissue to be stapled is clamped between the anvil and the body of the applicator. To permit this to be done, the anvil is movable toward and away from the applicator body. The minimum separation between the anvil and the body must be sufficiently small to clamp the tissue firmly but large enough not to crush the tissue. According to the preferred embodiment of the invention, this gap is adjustable. For this purpose, the flexible shaft comprises an outer sleeve (the relatively stiff sleeve referred to above) connecting the actuator and the body of the applicator and maintaining them irrotatable relative to each other, and a torsionally stiff but flexible inner sleeve one end of which is threadedly connected to a rod carrying the anvil for axial motion relative to the applicator body, the other end of the inner sleeve being secured to a rotatable portion of the actuator (preferably a dial) by means of which the inner sleeve can be rotated about its longitudinal axis. The inner sleeve may serve as the small-diameter tube or may contain a third tube for that purpose. The anvil rod is keyed irrotatably to the applicator body, so that rotation of the inner sleeve causes the anvil rod and the anvil to advance or retreat axially relative to the body of the applicator. This permits the surgeon to adjust the axial spacing between the anvil and the staple holder quite precisely by rotating the dial.

Other objects and features of the invention will become apparent from the following detailed description of one preferred embodiment, taken in conjunction with the accompanying figures, in which like reference characters refer throughout to like elements.

BRIEF DESCRIPTION OF THE FIGURES

FIG. 5 is a cross-sectional view from section line 5—5 of FIG. 1, showing the actuator mechanism before firing.

FIG. 6 is a cross-sectional view from section line 6—6 of FIG. 5.

FIG. 7 is a cross-sectional view similar to that of FIG. 5 showing the actuator mechanism during firing.

DETAILED DESCRIPTION OF THE PREFERRED EMBODIMENT

Figure 1:
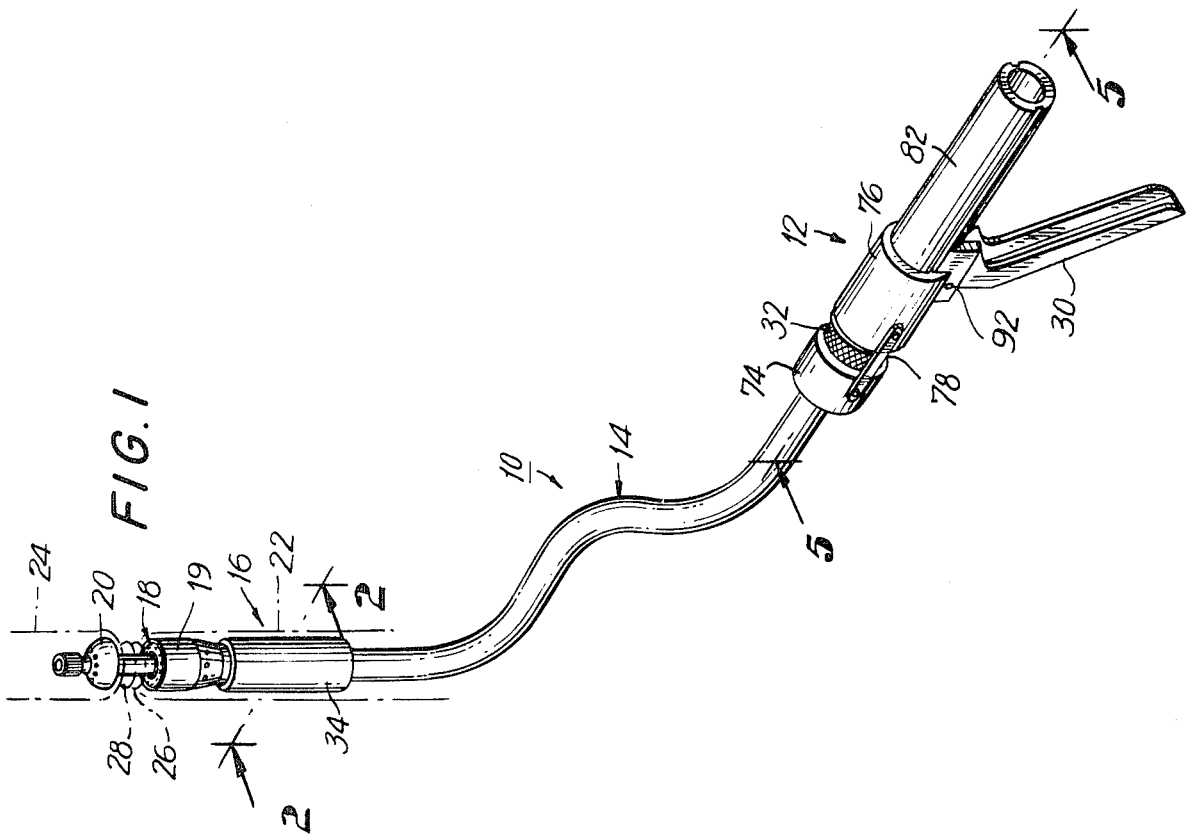
FIG. 1 is a perspective view of a device constructed according to the principles of the invention.

FIG. 1 shows the preferred embodiment of the apparatus 10 of the invention. In the embodiment shown, the apparatus is a surgical stapler for performing end-to-end anastomoses ("EEA"). The device includes an actuator 12, a flexible shaft 14 and an applicator 16, which in the illustrated embodiment is used with a standard staple cartridge 18. The cartridge 18 comprises a cartridge body 19, containing a staple holder, staple pushers and an annular knife, and an anvil 20.

In use, the applicator 16 is inserted into the lumen of the organ to be stapled (indicated in phantom at 22, 24), with the anvil 20 retracted more or less against the body of the cartridge 18 ("the closed position"). The insertion is preferably made via a natural orifice, so that no incision is required for insertion (as is sometimes the case with conventional EEA surgical staplers). When the instrument 10 is at the cut between the two organ sections 22, 24, the anvil 20 is extended to the open position (shown in FIG. 1) in a manner described below, and purse-string sutures 26, 28 are provided in both organ ends. The sutures 26, 28 are pulled tight, as shown in FIG. 1. The anvil 20 is then pulled closed to clamp the tissue 22, 24 against the cartridge body 19, and the surgeon actuates the device 10 by squeezing the handle 30. This staples the two organ sections 22, 24 together by means of a circumferential ring of staples and cuts out an annulus of tissue in the interior of the ring of staples. The annulus of tissue, which contains the sutures, is retained between the anvil 20 and the cartridge body 19 and is withdrawn from the organ 22 with the stapler 10.

When the anvil 20 is in the closed position, it must be close enough to the cartridge body 19 to clamp the tissue firmly but not so close as to crush the tissue. A dial 32 is provided in the actuator 12 to permit adjustment of the gap as described below.

Figure 2:
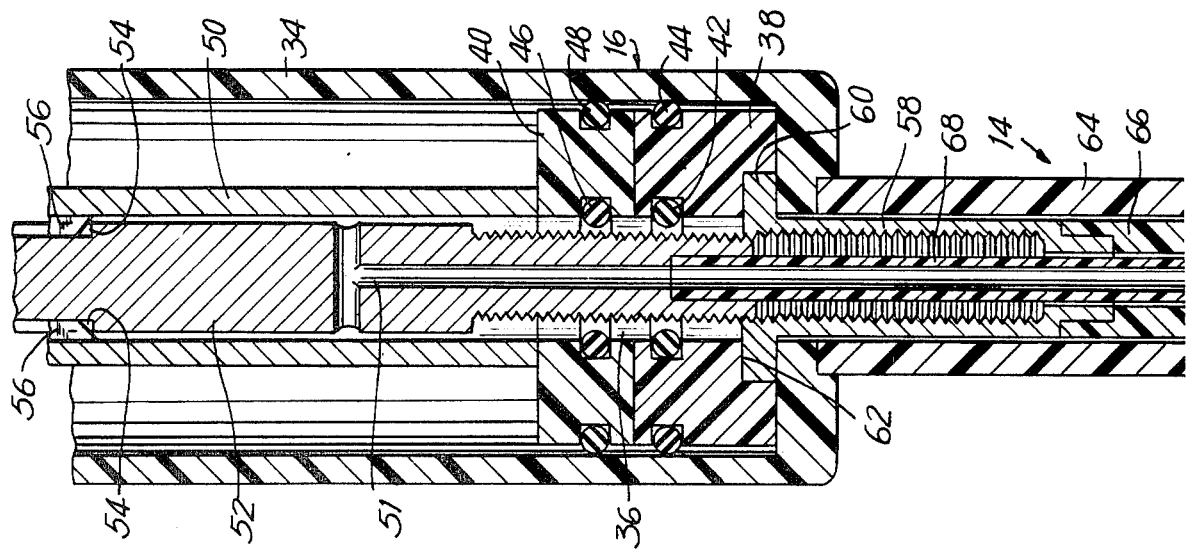
FIG. 2 is a cross-section of the device of FIG. 1, taken from section line 2—2 of FIG. 1, showing the applicator structure before firing.

FIG. 2 shows the applicator 16 in detail. The applicator 16 comprises a body 34 in which are slidably received two coaxial annular pistons 38, 40, each of which has an O-ring 42, 44, 46, 48 provided in a groove in each circumferential surface. The volume between the pistons 38, 40 defines a fluid chamber 36, which consists, at its smallest, of the space between the inner O-rings 42, 46 and, at its largest, of the space 36 indicated in FIG. 3.

The distal piston 40 has disposed on its distal surface a cylindrical sleeve 50. The distal end (not shown) of sleeve 50 is operatively connected to actuate the staple pushers of the cartridge 18 in a known manner to expel the staples from the cartridge 18 and clinch them against the anvil 20, and to drive the annular knife of the cartridge 18 to cut the annulus of tissue surrounded by the ring of staples.

An anvil rod 52 passes through the bore of the pistons 38, 40 and through the staple sleeve 50 and has its distal end (not shown) secured to the anvil 20 in known fashion. The anvil rod 52 has paraxial keyways 54 which receive keys 56 which are disposed on the cartridge 18 and extend down through the interior of the staple sleeve 50, to maintain rotational alignment between the staples contained in the cartridge 18 and the staple-clinching buckets (not shown) of the anvil 20. A T-shaped conduit 51 is provided in the anvil rod 52 for a purpose described below. The proximal end of the anvil rod 52 is threadedly received in the bore of a flanged collar 58, which extends into the flexible shaft 14. The flange 60 of the collar 58 is received on a shoulder 62 formed in the proximal surface of the proximal piston 38 and rests on the proximal end wall of the applicator body 34; however, the flanged collar 58 is free to rotate relative to both piston 38 and the applicator body 34.

The flexible shaft 14 includes three sleeves 64, 66 and 68. One end of the outer sleeve 64 is secured to the actuator 12, and the other end is fixed to the applicator body 34. The distal end of the middle sleeve 66 is secured, as by gluing, to the proximal end of the flanged collar 58. The proximal end of sleeve 66 is secured to the actuator dial 32. The distal end of the inner sleeve or tube 68 passes through the bore of the flange collar 58 and is secured to the proximal end of the anvil rod 52. The interior of tube 68 communicates with the stem of the T-shape conduit 51. The proximal end of tube 68 is attached to the actuator 32 in a manner shown in FIG. 5 and described below.

FIGS. 5 and 6 show the actuator 12 before firing. The actuator 12 comprises a two-part cylindrical body 72 whose sections 74, 76 are rigidly connected by two bars or bridges 78. The dial 32 for adjusting the anvil gap is rotatably disposed between the two parts 74, 76 by means of distal and proximal axial annular flanges 77, 79 received in parts 74, 76, respectively. The proximal end of outer sleeve 64 is fixedly received in a bore 75 in the distal end of the first part, or dial-hose attachment, 74.

The middle sleeve 66 passes through the dial-hose attachment 74 and has its proximal end fixed to the dial 32. Rotation of the dial 32 rotates flanged collar 58, moving the anvil 20 axially (the anvil 20 cannot rotate, since anvil rod 52 is keyed to the cartridge 18 via sleeve 50). For this purpose, sleeve 66 must be made of a torsionally stiff, yet flexible, material.

A fluid actuating cylinder 82 is slidably received in the open proximal end of the second part, or dial slide, 76. A fluid reservoir 84 is defined between the distal wall of fluid actuating cylinder 82 and a piston 86 slidably received in the fluid actuating cylinder 82. The inner sleeve or tube 68 is received slidably in a second bore 73 in the dial-hose attachment 74, in a longitudinal bore in the dial 32 and in an aperture in the distal wall 80 (not shown) of the dial slide 76. The proximal end of sleeve 68 is received fixedly in an aperture 87 in the distal wall of the fluid actuating cylinder 82. O-rings 88, 90 prevent leakage from the proximal end of reservoir 84. The handle 30, mounted pivotally on a dowel pin 92 secured to the actuator body 12, has cams 94 (only one of which is shown) received in a recess 96 in the shaft 98 of the piston 86.

Operation

As described above, the applicator 16 is moved to the cut to be stapled with the anvil 20 closed. The anvil 20 is then opened, by rotating the dial 32 until the threads of anvil rod 52 disengage from those of flanged collar 58, after which the surgeon pushes forward (distally) on the fluid actuating cylinder 82, causing the tube 68 to move the anvil 20 to the open position. After the sutures 26, 28 are in place and have been tightened, the surgeon closes anvil 20 by pulling the fluid actuating cylinder 82 until the anvil rod threads are able to engage those of flanged collar 58. Dial 32 is then rotated to adjust the gap between anvil 20 and cartridge body 19 to exactly the desired value. The stapler 10 is then fired.

To fire the stapler 10, the surgeon squeezes the handle 30 as indicated in FIG. 7, forcing the piston 86 forward, and forcing fluid from the reservoir 84 into the inner sleeve 68, from which it enters the fluid chamber 36 of the applicator 16.

Figure 4:
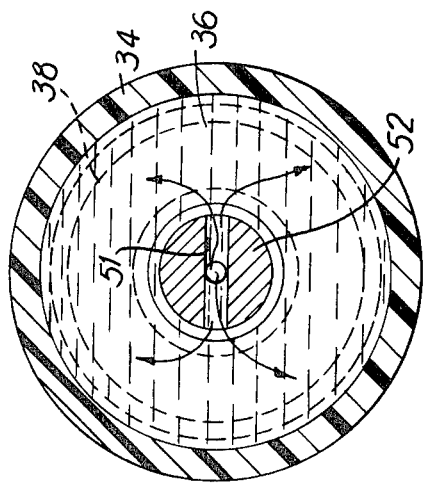
FIG. 4 is a cross-sectional view from section line 4—4 of FIG. 3.
Figure 3:
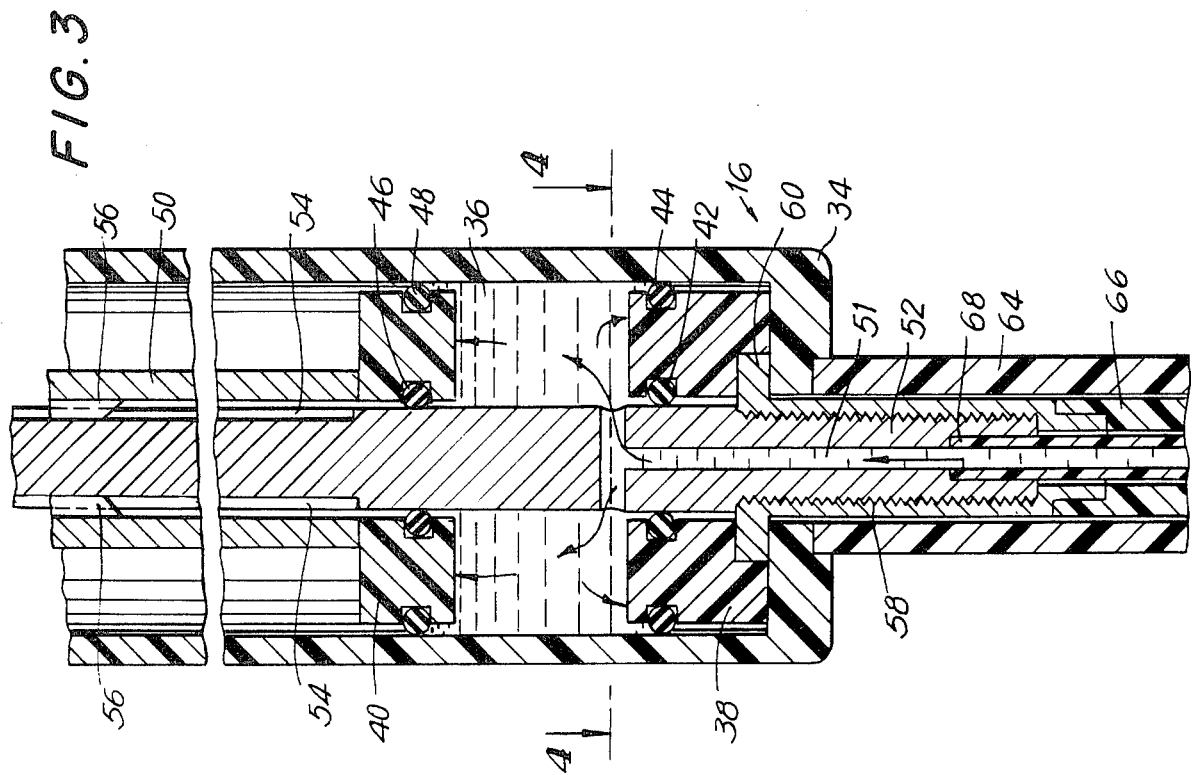
FIG. 3 is a cross-sectional view similar to that of FIG. 2, showing the device during firing.

FIGS. 3 and 4 show the applicator 16 during firing of the staples of cartridge 18. Movement of the anvil 20 to the closed position brings the transverse part of the T-shaped conduit 51 into axial alignment with the interface between pistons 38 and 40, and fluid is forced by piston 86 from the reservoir 84, through the inner sleeve 68 and the T-shaped conduit 51, and into the fluid chamber 36 defined between the inner O-rings 42, 46 (see FIG. 2). The fluid forces the distal piston 40 away from piston 38, driving the staple sleeve 50 to expel the staples from the cartridge body 19 and to clinch them against the anvil 20, and to power the annular knife to cut the tissue within the ring of staples. Piston 38 holds flanged collar 58 against the proximal wall of application body 34 during firing. As can be understood from FIG. 3, the forces of the stapling and cutting operation are absorbed by the flanged collar 58 and the applicator body 34, and are not transmitted along the flexible shaft 14. The only force tending to straighten the shaft 14 is the line tension due to the hydraulic fluid under pressure in tube 68. Because the diameter of tube 68 is much less than those of fluid chamber 36 and resevoir 84, this line tension is virtually negligible. In one model, a hydaulic pressure of 600 p.s.i., sufficient to staple and cut tissue successfully, produced a line tension of only 1.5 lb. in tube 68, whose inner diameter was 0.058 inch.

After stapling, the instrument 10 is withdrawn from the organ 22.

Thus the difference in diameter between the inner sleeve 68 and the fluid chambers 36, 84 makes the fluid pressure in the inner sleeve 68 extremely small, so that there is no sufficient straightening force in the inner sleeve 68.

In the preferred embodiment, the effective area of piston 86 is the same as that of pistons 38, 40; however, piston 86 could be made to have an effective area different from that of pistons 38, 40 to vary the mechanical advantage of the apparatus 10.

Although the present invention has been described particularly with reference to one preferred embodiment, many modifications and variations of that embodiment will now be apparent to those skilled in the art, and the scope of the invention is therefore to be limited not by the details described herein, but only by the terms of the appended claims.

I claim:

1. An apparatus for applying surgical fasteners, said apparatus comprising:
   applicator means for applying fasteners to tissue; said applicator means including applying means and anvil means for cooperating with said applying means to apply the fasteners to tissue;
   actuator means for actuating said applicator means to apply fasteners to tissue; and
   shaft means connecting said applicator means and said actuator means, said shaft means being substantially flexible to bend during insertion into a body channel to conform to the configuration of the body channel into which the apparatus is inserted for the particular surgical operation being performed and capable of retaining said configuration during actuation; said shaft means being for transmitting a first, relatively small force from said actuator means to said applicator means hydraulically, and comprising first and second sleeves, said first sleeve being within said second sleeve, and said actuator means comprising slide means secured to said first sleeve for moving said anvil means toward or away from said applying means; said applicator means being for producing, responsive to said first force, a second force larger than said first force, for applying the fasteners to tissue; and said applicator means further comprising means for hydraulically maintaining a selected gap between said anvil means and said applying means during application of the fasteners to tissue.

2. The apparatus of claim 1, wherein said applicator means transmits said second force by means of fluid pressure.

3. The apparatus of claim 2, wherein said fluid pressure is hydraulic pressure.

4. The apparatus of claim 3, wherein a 0.9 percent sterile saline solution is used as the hydraulic fluid for transmitting said forces.

5. The apparatus of claim 1, wherein said applicator means comprises a first fluid chamber, and said actuator means is for applying said first force to increase the fluid pressure in said first fluid chamber to produce said second force.

6. The apparatus of claim 5, wherein said actuator means comprises a second fluid chamber communicating with said first fluid chamber via said shaft means;

said actuator means further comprising means for increasing the fluid pressure in said second fluid chamber to actuate said apparatus; said first and second fluid chambers having, respectvely, first and second diameters greater than the diameter of the portion of said shaft means that communicates with said fluid chambers, whereby said first force is less than said second force.

7. The apparatus of claim 1, wherein said anvil means is irrotatable relative to said applying means and said first sleeve is attached to said anvil means.

8. The apparatus of claim 7, further comprising flanged collar means, wherein said first sleeve has one end threadedly attached to said anvil means via said flanged collar means to allow rotation of said first sleeve relative to said anvil means and for adjusting the axial position of said anvil means relative to said applying means; said second sleeve connecting said applying means to said actuator means; and said actuator means comprising dial means secured to the other end of said first sleeve for rotating said first sleeve to adjust the position of said anvil means.

9. The apparatus of claim 8, wherein said applicator means includes a first fluid chamber containing a first piston for applying said second force to said applying means, and wherein said maintaining means disposed in said first fluid chamber comprises a second piston for maintaining said flanged collar means and said anvil means stationary relative to said applying means during application of the fasteners.

10. An apparatus for applying surgical fasteners, said apparatus comprising:
applicator means for applying fasteners to tissue; said applicator means including applying means and anvil means for cooperating with said applying means, to apply the fasteners to tissue;
actuator means for actuating said applicator means to apply fasteners to tissue;
shaft means connecting said applicator means and said actuator means, said shaft means being substantially flexible to bend during insertion into a body channel to conform to the configuration of the body channel into which the apparatus is inserted for the particular surgical operation being performed and capable of retaining said configuration during actuation; said shaft means being for transmitting a first, relatively small force from said actuator means to said applicator means hydraulically and comprising first and second sleeves, said first sleeve being within said second sleeve, and said actuator means comprising slide means secured to said fist sleeve for moving said anvil means toward or away from said applying means; said applicator means being for producing, responsive to said first force, a second force larger than said first force, for applying the fasteners to tissue; and
said actuator means further comprising means for mechanically adjusting the spacing between said anvil means and said applying means.

11. An apparatus for applying a surgical fastener to tissue, said apparatus comprising:
an anvil assembly;
a fastener-holding assembly containing a surgical fastener, said fastener-holding assembly including (a) a first body, (b) anvil support means for supporting said anvil assembly for motion relative to said first body to allow tissue that is to be fastened to be clamped between said first body and said anvil assembly, and (c) pusher means mounted movably relative to said first body for driving a fastener from said fastener-holding assembly through the clamped tissue toward said anvil assembly;
an actuator assembly remote from said fastener-holding assembly and including (a) a second body, (b) first actuator means movably mounted on said second body for controlling said anvil support means, and (c) second actuator means movably mounted on said second body for controlling said pusher means; and
a longitudinal shaft assembly being substantially flexible to bend during insertion into a body channel to conform to the configuration of the body channel into which the apparatus is inserted for the particular surgical operation being performed, said shaft assembly including (a) a flexible outer member having one end connected to said first body and having a second end connected to said second body, (b) first flexible force transmitting means disposed in said outer member for transmitting force from said first actuator to control movement of said anvil assembly, and (c) second flexible force transmitting means disposed in said outer member for transmitting force from said second actuator to control said pusher means for driving a fastener from said fastener-holding assembly toward said anvil assembly.

* * * * *